United States Patent
Zhu et al.

(10) Patent No.: US 7,705,593 B1
(45) Date of Patent: Apr. 27, 2010

(54) APPARATUS AND METHOD FOR DETECTING AND CLASSIFYING ATHEROSCLEROTIC PLAQUE HEMORRHAGE

(75) Inventors: David C. Zhu, East Lansing, MI (US); J. Kevin DeMarco, Okemos, MI (US); Anthony T. Vu, Waukesha, WI (US)

(73) Assignees: General Electric Company, Schenectady, NY (US); The Board Of Trustees Of Michigan State University, East Lansing, MI (US)

( * ) Notice: Subject to any disclaimer, the term of this patent is extended or adjusted under 35 U.S.C. 154(b) by 0 days.

(21) Appl. No.: 12/254,630

(22) Filed: Oct. 20, 2008

(51) Int. Cl.
*G01V 3/00* (2006.01)
(52) U.S. Cl. ...................... 324/306; 600/411
(58) Field of Classification Search .............. 324/306, 324/309; 600/411
See application file for complete search history.

(56) References Cited

U.S. PATENT DOCUMENTS

| | | | |
|---|---|---|---|
| 6,489,766 B1 * | 12/2002 | Alsop | 324/313 |
| 7,315,756 B2 * | 1/2008 | Yarnykh et al. | 600/411 |
| 7,474,097 B2 * | 1/2009 | Bydder et al. | 324/307 |

OTHER PUBLICATIONS

Moody et al., "Characterization of Complicated Carotid Plaque With Magnetic Resonance Direct Thrombus Imaging in Patients With Cerebral Ischemia," Circulation Journal of the American Heart Association, 2003.

Zhu et al., "An optimized 3D inversion recovery prepared fast spoiled gradient recalled sequence for carotid plaque hemorrhage imaging at 3.0 T," ScienceDirect, Magnetic Resonance Imaging, Published Online at www.sciencedirect.com, Jun. 2008.

Zhu et al., "An Optimized 3D Inversion Recovery Prepared Fast Spoiled Gradient Recalled Sequence with Multiple Echoes (IR FSPGR ME) for Carotid Plaque Imaging," Proc. Intl. Soc. Mag. Reson. Med., vol. 16, 2008, p. 2841.

* cited by examiner

*Primary Examiner*—Louis M Arana
(74) *Attorney, Agent, or Firm*—Ziolkowski Patent Solutions Group, SC

(57) ABSTRACT

A system and method for detecting atherosclerotic plaque hemorrhage includes a controller programmed to apply a non-selective inversion recovery RF pulse to a region of interest, apply a plurality of encoding sequences to the region of interest to cause generation of a plurality of echoes during application of each encoding sequence. The controller is further programmed to acquire three dimensional MR data from the region of interest during generation of each of the plurality of echoes, identify a hemorrhage based on the three dimensional MR data, characterize a type of the hemorrhage, and reconstruct an image based on the three dimensional MR data, the image comprising the characterized hemorrhage.

19 Claims, 4 Drawing Sheets

APPARATUS AND METHOD FOR DETECTING AND CLASSIFYING ATHEROSCLEROTIC PLAQUE HEMORRHAGE

BACKGROUND OF THE INVENTION

The invention relates generally to magnetic resonance (MR) imaging and, more particularly, to an apparatus and method for detecting and classifying atherosclerotic plaque hemorrhage.

When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Carotid plaque hemorrhage has been associated with increased plaque progression and increased risk of future stroke/transient ischemic attacks. Detection, identification, and classification of atherosclerotic plaque hemorrhage may allow a treatment plan to be developed for a patient having an atherosclerotic plaque hemorrhage such that negative risks associated therewith may be minimized.

It would therefore be desirable to have a system and method capable of detecting and classifying atherosclerotic plaque hemorrhage.

BRIEF DESCRIPTION OF THE INVENTION

In accordance with one aspect of the invention, a magnetic resonance (MR) imaging apparatus includes a plurality of gradient coils positioned about a bore of a magnet, and an RF transceiver system controlled by a pulse module to transmit RF signals to an RF coil assembly. A controller is included and programmed to apply a non-selective inversion recovery RF pulse to a region of interest and to apply a plurality of encoding sequences to the region of interest to cause generation of a plurality of echoes during each encoding sequence. The computer is further programmed to acquire three dimensional MR data from the region of interest during generation of each of the plurality of echoes, identify a hemorrhage based on the three dimensional MR data, characterize a type of the hemorrhage, and reconstruct an image based on the three dimensional MR data, the image comprising the characterized hemorrhage.

In accordance with another aspect of the invention, a method for detecting an atherosclerotic plaque hemorrhage includes applying a non-selective inversion recovery RF pulse toward a subject to be imaged, generating a plurality of echoes from the subject during each of a plurality of encoding sequences, and acquiring magnetic resonance (MR) data during generation of each echo. The method also includes generating a three dimensional MR data set from the acquired MR data, identifying and characterizing a hemorrhage based on the three dimensional MR data set, and generating an image showing the hemorrhage.

In accordance with another aspect of the invention, a computer readable storage medium having stored thereon a computer program comprising instructions, which when executed by a computer, cause the computer to apply a non-selective inversion recovery RF pulse to a region of interest and apply a plurality of multi-echo encoding sequences to the region of interest. The computer is further caused to acquire magnetic resonance (MR) data from a plurality of echoes generated in the region of interest during each multi-echo encoding sequence, locate and classify hemorrhage information based on the acquired MR data, and reconstruct an image comprising the located hemorrhage.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Figure 1:
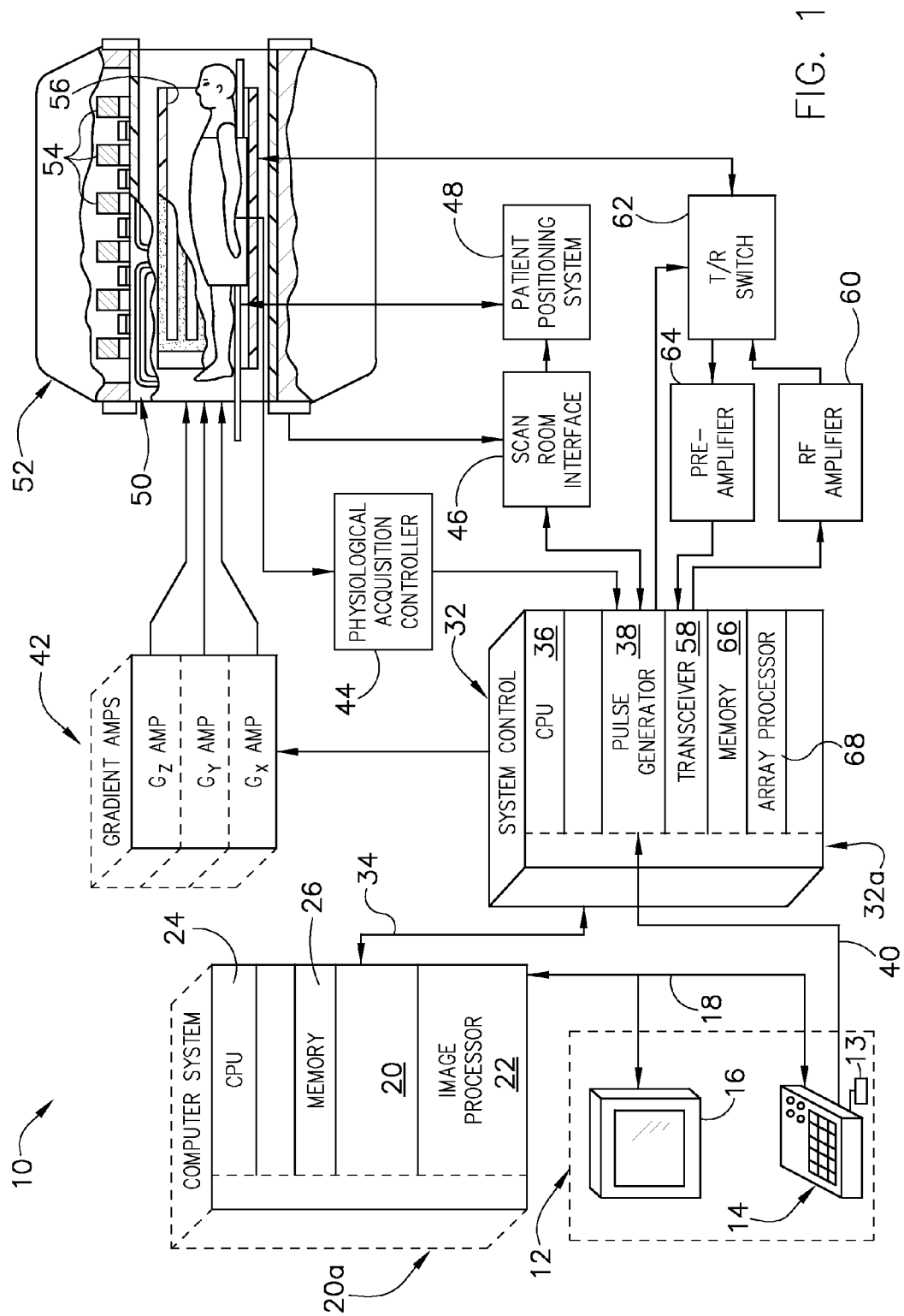
FIG. 1 is a schematic block diagram of an exemplary MR imaging system for use with embodiments of the invention.

Referring to FIG. 1, the major components of a preferred magnetic resonance imaging (MRI) system 10 incorporating an embodiment of the invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26 that may include a frame buffer for storing image data arrays. The computer system 20 communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a resonance assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Figure 2:
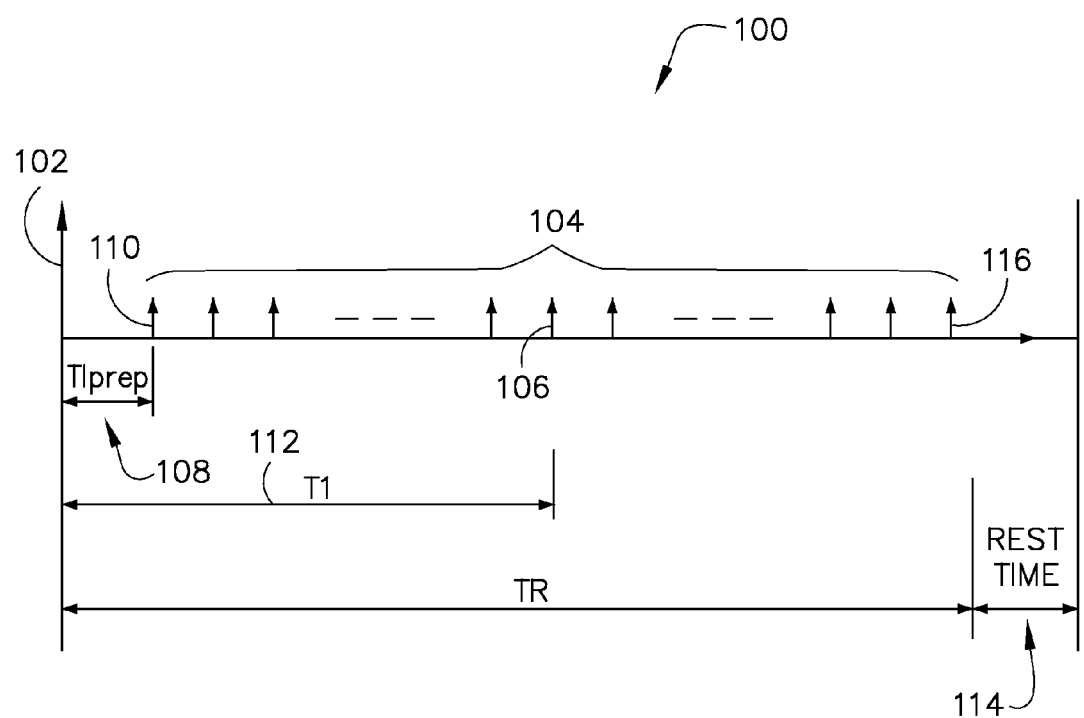
FIG. 2 is an imaging sequence diagram according to an embodiment of the invention.

FIG. 2 shows an imaging sequence diagram according to an embodiment of the invention. Sequence 100 illustrates an Inversion Recovery prepared Fast SPoiled Gradient Recalled sequence with Multiple Echoes (IR FSPGR ME). Sequence 100 includes a non-selective inversion recovery (IR) RF pulse 102 followed by a plurality of multi-echo encoding sequences 104, each encoding sequence having a plurality of pulses designed to excite multiple echoes from a region of interest as discussed below with respect to FIG. 3. Fat suppression technique (chemical selective saturation, water-excitation, n-points Dixon decomposition, etc.) can be employed to suppress signal contribution from fat. In an embodiment of the invention, sequence 100 is a three-dimensional (3D), T1-weighted imaging sequence, and encoding sequences 104 are arranged according to an ordering sequence. For example, as shown, encoding sequences 104 are arranged according to a sequential slice encoding ordering sequence such that an encoding sequence 106 that acquires data for a central region of k-space is centrally positioned among the plurality of encoding sequences 104.

A delay 108 (e.g., a TIprep delay) between application of non-selective IR RF pulse 102 and a first encoding sequence 110 of the plurality of multi-echo encoding sequences 104 may be calculated to optimally determine and select a time of inversion (TI) 112 such that signals from blood are suppressed. A rest time 114 after application of a last encoding sequence 116 of the plurality of multi-echo encoding sequences 104 may be optimally determined and selected along with the time of inversion 112 to further minimize signal from a blood flow during MR data acquisition to increase contrast between, for example, a vessel lumen (not shown) and a vessel wall (not shown).

It is contemplated that other ordering sequences may be used to order encoding sequences 104 instead of the sequential slice encoding ordering sequence shown in FIG. 2. For example, according to other embodiments of the invention, encoding sequences 104 may be ordered according to another desired ordering sequence such as a centric slice encoding ordering sequence, a sequential phase encoding ordering sequence, a centric phase encoding ordering sequence, and elliptical centric ordering sequence, or a radial fan beam centric encoding ordering sequence. As such, the position of encoding sequence 106 may vary according to the desired encoding ordering sequence.

Figure 3:
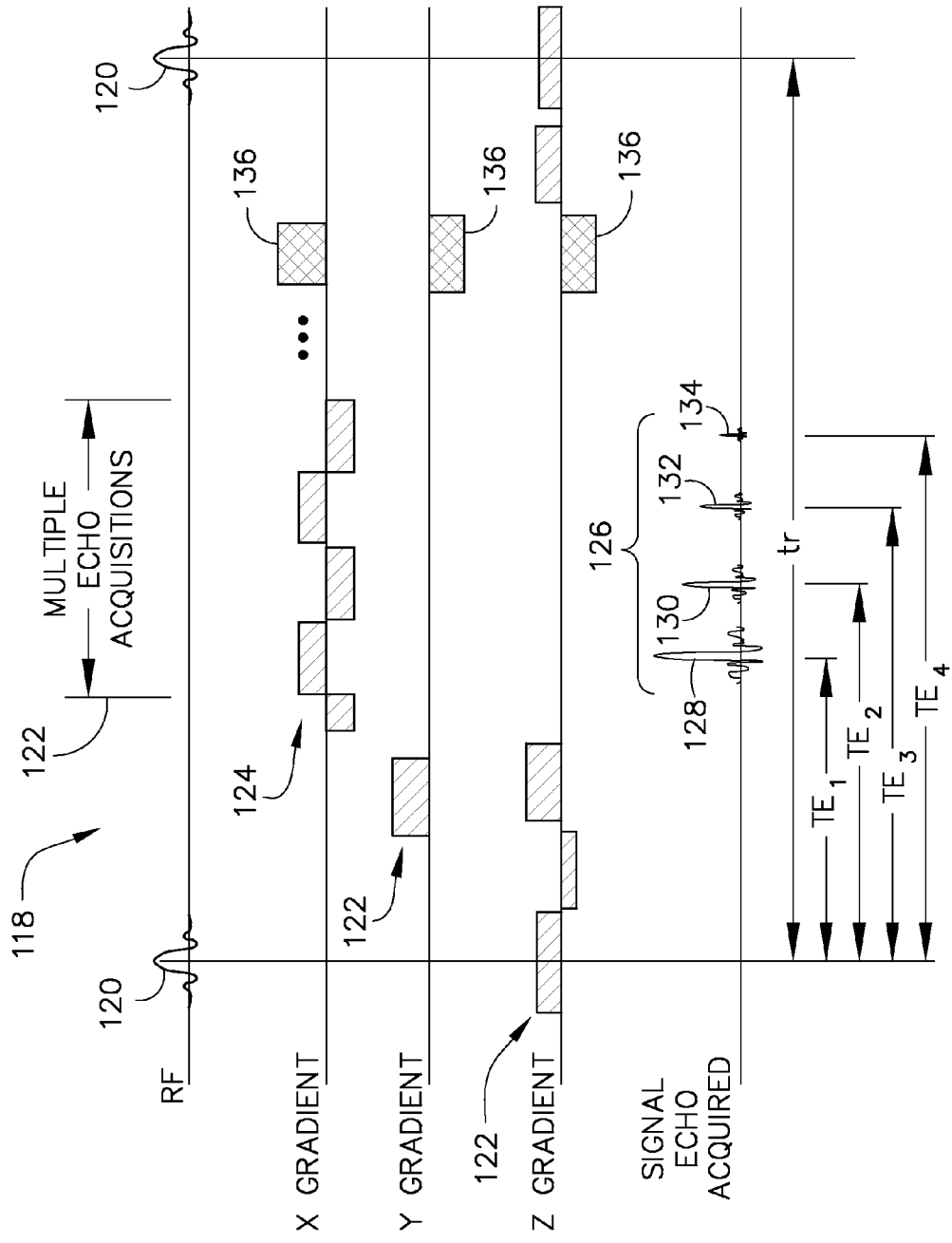
FIG. 3 is a multi-echo acquisition pulse sequence diagram according to an embodiment of the invention.

FIG. 3 shows a multi-echo acquisition pulse sequence 118 according to an embodiment of the invention. Pulse sequence 118 illustrates pulses to be generated in each of the encoding sequences 104 illustrated in FIG. 1. Following the application of an RF pulse 120 and Y and Z gradient pulses 122, a plurality of readout gradients 124 allow acquisition of MR signal data from a multi-echo acquisition 126 having a plurality of echoes 128, 130, 132, 134 excited from a region of interest. The MR signal data from each echo 128-134 contribute to a respective full 3D k-space MR data set. That is, MR signal data from echo 128 contribute to a first 3D k-space MR data set (not shown), MR signal data from echo 130 contribute to a second 3D k-space MR data set (not shown), MR signal data from echo 132 contribute to a third 3D k-space MR data set (not shown), and MR signal data from echo 134 contribute to a fourth 3D k-space MR data set (not shown). Embodiments of the invention may include acquiring MR data from two, three, four, or more echoes in multi-echo acquisition 126. Accordingly, a respective two, three, four, or more 3D k-space MR data sets may be filled.

A plurality of spoiler gradients 136 may be applied after acquiring MR data from echoes 128-134 to destroy transverse magnetization prior to application of a next excitation pulse 120. However, while FIGS. 2 and 3 show an IR FSPGR ME sequence, it is contemplated that an IR non-spoiled prepared gradient recalled echo sequence, combined with multi-echo acquisition as described above, may be used to suppress signals from blood instead. Alternatively, it is contemplated that a Steady State Free Precession (SSFP) sequence or a Balanced Steady State Free Precession (b-SSFP) sequence, combined with multi-echo acquisition as described above, may instead be used to suppress signals from blood. While FIG. 3 shows an implementation of multi-echo acquisition using a bi-polar read-out gradient, it is contemplated that a unipolar read-out gradient may also be used for multi-echo acquisition according to an embodiment of the invention.

Referring to FIGS. 2 and 3, each application of multi-echo acquisition pulse sequence 118 results in the filling of one line of each 3D k-space MR data set. For example, according to one embodiment of the invention, each application of sequence 118 results in the filling of one line of each of the first, second, third, and fourth 3D k-space MR data sets using data acquired from echoes 128-134, respectively. Each application of sequence 100 may result in, for example, the filling of a complete slice of MR data for each of the first, second, third, and fourth 3D k-space MR data sets. Sequence 100 is repeatedly applied to a region of interest for acquiring and filling a complete first, second, third, and fourth 3D MR data set corresponding to matrix size.

Figure 4:
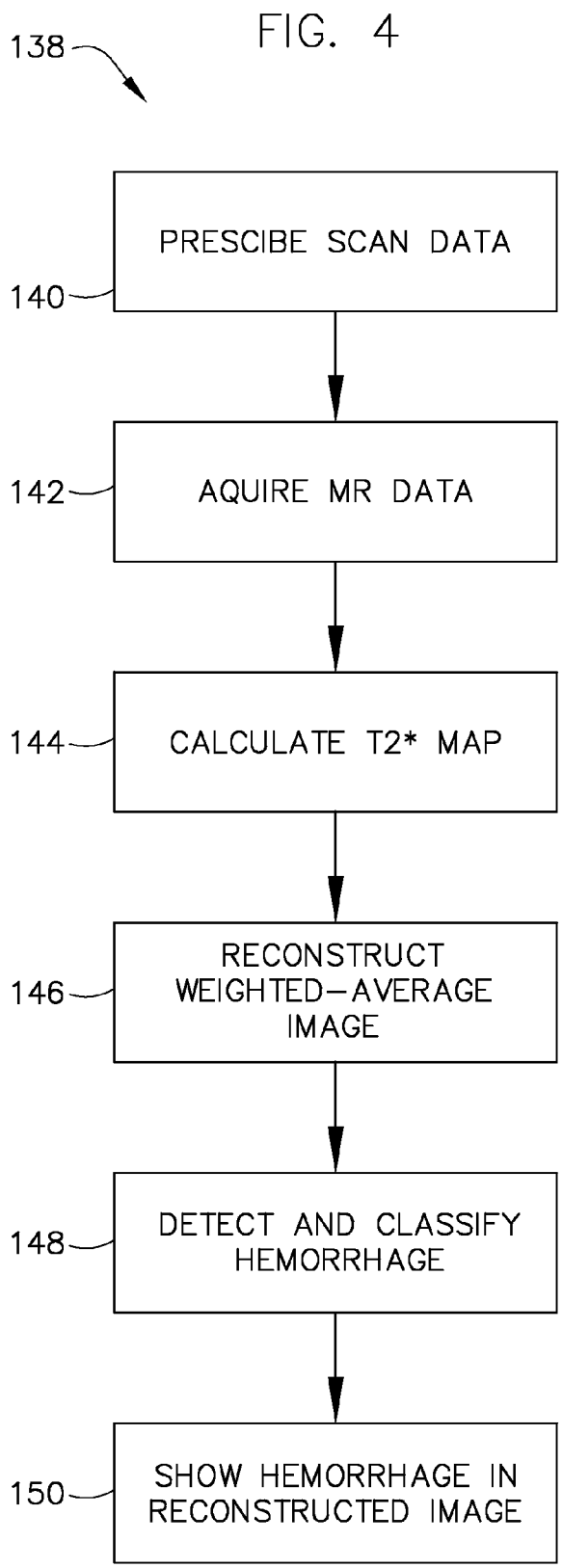
FIG. 4 is a flowchart showing a technique for detecting and classifying an atherosclerotic plaque hemorrhage according to an embodiment of the invention.

FIG. 4 shows a technique 138 for detecting and classifying an atherosclerotic plaque hemorrhage according to an embodiment of the invention. Technique 138 begins at block 140 with prescribing scan data. Prescribing scan data includes determining pulse sequence parameters for the pulse sequence(s) to be used, for example, the pulse sequences 100, 118 shown in FIGS. 2 and 3. Determining the pulse sequence parameters can include, for example, determining an encoding sequence, such as those described above, for the plurality of multi-echo encoding sequences 104 and determining a time of inversion 112 such that signals from blood are suppressed during MR data acquisition. A delay 108 may also be prescribed to appropriately select the time of inversion 112 for the determined encoding sequence. Furthermore, a rest time 114 may also be prescribed to further minimize signal from a blood flow during MR data acquisition as described above. Prescribing scan data also includes determining a number of signals to be acquired in multi-echo acquisition 126 from the imaging subject. As described above, the number of signals to be acquired in multi-echo acquisition 126 relates to the number of 3D, T1-weighted k-space MR data sets to be filled.

Following the prescription of scan data at block 140, MR data is acquired from a region of interest at block 142 via the application of the pulse sequences 100, 118 (shown in FIGS. 2 and 3) for which the parameters have been prescribed at block 140. For example, the pulse sequences prescribed at block 140 are applied according to the prescribed scan data. A T2* map is calculated at block 144 based on the semi-log linear regression of the voxel signal values and the corresponding echo times (TE), such as $TE_1$, $TE_2$, $TE_3$, and $TE_4$ shown in FIG. 3, according to the equation:

$$1/T2^* = -[(lnS_n - lnS_m)/(TE_n - TE_m)] \quad \text{(Eqn. 1)},$$

where $S_n$ and $S_m$ are voxel signal intensity at TE values of $TE_n$ and $TE_m$, respectively.

A weighted-average image is reconstructed at block 146 for the number of 3D, T1-weighted MR data sets that have been filled. Weighted-averaging includes calculating a signal weighted average, $S_{ave}$, for each voxel in the weighted-average image according to:

$$\sum_{i=1}^{m} \left( S_i \times \left( \frac{S_i}{\sum_{j=1}^{m} S_j} \right) \right), \quad \text{(Eqn. 2)}$$

where m is the number of the plurality of echoes and where $S_i$ and $S_j$ represent the signal at $TE_i$ and $TE_j$, respectively. For example, obtaining the signal weighted average, $S_{ave}$, from a two-echo sequence according to Eqn. 2 may be calculated by:

$$S_{ave} = S_1 \times (S_1/(S_1+S_2)) + S_2 \times (S_2/(S_1+S_2)) \quad \text{(Eqn. 3)},$$

For a three-echo sequence, obtaining the signal weighted average, $S_{ave}$, according to Eqn. 2 may be calculated by:

$$S_{ave} = S_1 \times (S_1/(S_1+S_2+S_3)) + S_2 \times (S_2/(S_1+S_2+S_3)) + S_3 \times (S_3/(S_1+S_2+S_3)) \quad \text{(Eqn. 4)}.$$

The weighted averaging helps to increase signal-to-noise ratio (SNR) of the reconstructed image and emphasizes the signal at $TE_i$, or at the first echo, to maintain the ability of hemorrhage detection.

At block 148, a hemorrhage in the reconstructed weighted-average image is detected and classified or characterized based on the calculated T2* map. According to an embodiment of the invention, a hemorrhage is classified as a Type I hemorrhage, a Type II hemorrhage, or a non-Type I hemorrhage. A Type I hemorrhage has been correlated with, for example, ipsilateral carotid symptoms. Following classification of the hemorrhage, the hemorrhage is shown at block 150 in the reconstructed weighted-average image to a user. In one embodiment, the hemorrhagic region may be identified or highlighted with T2* color coding scheme overlaid with the reconstructed image.

According to an embodiment of the invention, computer system 20 of FIG. 1 may be programmed according to technique 138 for the automatic detection and classification of hemorrhages. However, it is contemplated that a computer remote from MR system 10 as shown in FIG. 1 may also be similarly programmed.

Embodiments of the invention allow for the detection and characterization of hemorrhage types in one sequence, which may be referred to as optimized 3D Spoiled gradient for Hemorrhage assessment using INversion recovery and multiple Echoes (3D SHINE). Accordingly, scan time efficiency is improved, and image mis-registration may be eliminated. Plaque visualization is also improved due to an improved SNR achieved through embodiments of the invention.

In accordance with one embodiment of the invention, a magnetic resonance (MR) imaging apparatus includes a plurality of gradient coils positioned about a bore of a magnet, and an RF transceiver system controlled by a pulse module to transmit RF signals to an RF coil assembly. A controller is included and programmed to apply a non-selective inversion recovery RF pulse to a region of interest and to apply a plurality of encoding sequences to the region of interest to cause generation of a plurality of echoes during each encoding sequence. The computer is further programmed to acquire three dimensional MR data from the region of interest during generation of each of the plurality of echoes, identify a hemorrhage based on the three dimensional MR data, characterize a type of the hemorrhage, and reconstruct an image based on the three dimensional MR data, the image comprising the characterized hemorrhage.

In accordance with another embodiment of the invention, a method for detecting an atherosclerotic plaque hemorrhage includes applying a non-selective inversion recovery RF pulse toward a subject to be imaged, generating a plurality of echoes from the subject during each of a plurality of encoding sequences, and acquiring magnetic resonance (MR) data during generation of each echo. The method also includes generating a three dimensional MR data set from the acquired MR data, identifying and characterizing a hemorrhage based on the three dimensional MR data set, and generating an image showing the hemorrhage.

In accordance with another embodiment of the invention, a computer readable storage medium having stored thereon a computer program comprising instructions, which when executed by a computer, cause the computer to apply a non-selective inversion recovery RF pulse to a region of interest and apply a plurality of multi-echo encoding sequences to the region of interest. The computer is further caused to acquire magnetic resonance (MR) data from a plurality of echoes generated in the region of interest during each multi-echo encoding sequence, locate and classify hemorrhage information based on the acquired MR data, and reconstruct an image comprising the located hemorrhage.

The invention has been described in terms of the preferred embodiment, and it is recognized that equivalents, alternatives, and modifications, aside from those expressly stated, are possible and within the scope of the appending claims.

What is claimed is:

1. A magnetic resonance imaging (MRI) apparatus comprising:
    a plurality of gradient coils positioned about a bore of a magnet, and an RF transceiver system controlled by a pulse module to transmit RF signals to an RF coil assembly; and
    a controller coupled to the plurality of gradient coils and the RF transceiver system and programmed to:
        apply a non-selective inversion recovery RF pulse to a region of interest;
        apply a plurality of encoding sequences to the region of interest to cause the generation of a plurality of echoes during each encoding sequence;
        acquire three dimensional magnetic resonance (MR) data from the region of interest;
        identify a hemorrhage based on the three dimensional MR data;
        characterize a type of the hemorrhage; and
        reconstruct an image based on the three dimensional MR data, the image comprising the characterized hemorrhage.

2. The MRI apparatus of claim 1 wherein identifying the hemorrhage comprises calculating a T2* mapping based on a semi-log linear regression of voxel signal values in the three dimensional MR data and from echo times corresponding to the voxel signal values.

3. The MRI apparatus of claim 2 wherein the T2* mapping is calculated using at least two echo time points and according to the relationship:

$$1/T2^* = -[lnS_n - lnS_m]/(TE_n - TE_m)],$$

where $S_n$ and $S_m$ are voxel signal intensity at TE values of $TE_n$ and $TE_m$, respectively.

4. The MRI apparatus of claim 2 wherein the controller is further programmed to characterize the hemorrhage based on the T2* mapping as one of a Type I hemorrhage, a Type II hemorrhage, and a non-Type I hemorrhage.

5. The MRI apparatus of claim 1 wherein reconstructing the image comprises reconstructing a weighted-average image based on the three dimensional MR data acquired from the plurality of echoes during application of each encoding sequence.

6. The MRI apparatus of claim 5 wherein reconstructing the weighted-average image comprises calculating a signal weighted average, $S_{ave}$, according to:

$$\sum_{i=1}^{m} \left( S_i \times \left( \frac{S_i}{\sum_{j=1}^{m} S_j} \right) \right),$$

where m is the number of the plurality of echoes and where $S_i$ and $S_j$ represent the signal at $TE_i$ and $TE_j$, respectively.

7. The MRI apparatus of claim 1 wherein the controller is further programmed to delay a predetermined time between applying the non-selective inversion recovery RF pulse and applying a first of the plurality of encoding sequences.

8. The MRI apparatus of claim 7 wherein the controller is further programmed to calculate the predetermined time based on a time between applying the non-selective inversion recovery RF pulse and apply an encoding sequence of the plurality of encoding sequences configured to acquire MR data in a center of k-space such that signals from blood are suppressed in the region of interest.

9. The MRI apparatus of claim 1 wherein the controller is further programmed to determine an ordering sequence for the plurality of encoding sequences.

10. The MRI apparatus of claim 9 wherein determining the ordering sequence comprises determining one of a sequential encoding ordering sequence, a centric slice encoding ordering sequence, a sequential phase encoding ordering sequence, a centric phase encoding ordering sequence, and elliptical centric ordering sequence, and a radial fan beam centric encoding ordering sequence.

11. A method for detecting an atherosclerotic plaque hemorrhage comprising:
    applying a non-selective inversion recovery RF pulse toward a subject to be imaged;
    generating a plurality of echoes from the subject during each of a plurality of encoding sequences;
    acquiring magnetic resonance (MR) data during generation of each echo;
    generating a three dimensional MR data set from the acquired MR data;
    identifying and characterizing a hemorrhage based on the three dimensional MR data set, wherein identifying the hemorrhage comprises generating a T2* map from echo times corresponding to voxel signal values in the three dimensional MR data set and based on a semi-log linear regression of the voxel signal values; and
    generating an image showing the hemorrhage.

12. The method of claim 11 wherein generating the T2* map comprises calculating the T2* map based on a semi-log linear regression of multiple echo time points according to a relationship given by:

$$1/T2^* = -[(lnS_n - lnS_m)/(TE_n - TE_m)],$$

where $S_n$ and $S_m$ are voxel signal intensity at TE values of $TE_n$ and $TE_m$, respectively.

13. The method of claim 11 wherein generating the image comprises reconstructing a weighted-average image using a formula given by:

$$\sum_{i=1}^{m} \left( S_i \times \left( \frac{S_i}{\sum_{j=1}^{m} S_j} \right) \right),$$

where m is the number of the plurality of echoes and where $S_i$ and $S_j$ represent the signal at $TE_i$ and $TE_j$, respectively.

14. The method of claim 11 further comprising delaying a predetermined time between generating the non-selective inversion recovery RF pulse and generating a first echo during a first of the plurality of encoding sequences to suppress blood signals in the acquired MR data.

15. The method of claim 14 further comprising:
    delaying a predetermined rest time after generating a last echo during a last of the plurality of encoding sequences;

applying a second non-selective inversion recovery RF pulse toward the subject to be imaged after delaying the predetermined rest time;

generating a second plurality of echoes from the subject during each of a second plurality of encoding sequences;

acquiring MR data during generation of each echo of the second plurality of echoes; and filling a portion of the three dimensional MR data set with the MR data acquired during generation of each echo of the second plurality of echoes.

16. The method of claim 11 further comprising highlighting the hemorrhage in the image.

17. A computer readable storage medium having stored thereon a computer program comprising instructions, which when executed by a computer, cause the computer to:

apply a non-selective inversion recovery RF pulse to a region of interest;

apply a plurality of multi-echo encoding sequences to the region of interest;

acquire magnetic resonance (MR) data from a plurality of echoes generated in the region of interest during each multi-echo encoding sequence;

locate and classify hemorrhage information based on the acquired MR data; and reconstruct an image comprising the located hemorrhage.

18. The computer readable storage medium of claim 17 having further instructions to cause the computer to generate a T2* map based on a semi-log linear regression of multiple echo time points according to a relationship given by:

$$1/T2^* = -[(lnS_n - lnS_m)/(TE_n - TE_m)],$$

where $S_n$ and $S_m$ are voxel signal intensity at TE values of $TE_n$ and $TE_m$, respectively.

19. The computer readable storage medium of claim 18 wherein the instructions that cause the computer to classify hemorrhage information cause the computer to classify the located hemorrhage based on the T2* map as one of a Type I hemorrhage, a Type II hemorrhage, and a non-Type I hemorrhage.

* * * * *